United States Patent
Aso et al.

(10) Patent No.: US 11,798,692 B2
(45) Date of Patent: Oct. 24, 2023

(54) SYSTEMS AND METHODS FOR ASSISTED TRANSPORTATION FOR MEDICAL CARE

(71) Applicant: Toyota Research Institute, Inc., Los Altos, CA (US)

(72) Inventors: Makoto Aso, Ann Arbor, MI (US); Kazuyoshi Shiohara, Ann Arbor, MI (US)

(73) Assignee: Toyota Research Institute, Inc., Los Altos, CA (US)

( * ) Notice: Subject to any disclaimer, the term of this patent is extended or adjusted under 35 U.S.C. 154(b) by 949 days.

(21) Appl. No.: 16/213,247

(22) Filed: Dec. 7, 2018

(65) Prior Publication Data

US 2020/0185112 A1 Jun. 11, 2020

(51) Int. Cl.

| | |
|---|---|
| *G16H 80/00* | (2018.01) |
| *G06Q 10/1093* | (2023.01) |
| *G16H 40/63* | (2018.01) |
| *A61G 3/06* | (2006.01) |
| *A61B 5/00* | (2006.01) |
| *A61B 5/1172* | (2016.01) |
| *A61B 5/0205* | (2006.01) |

(Continued)

(52) U.S. Cl.
CPC ........... *G16H 80/00* (2018.01); *A61B 5/0006* (2013.01); *A61B 5/0008* (2013.01); *A61B 5/0013* (2013.01); *A61B 5/0022* (2013.01); *A61B 5/01* (2013.01); *A61B 5/02055* (2013.01); *A61B 5/1172* (2013.01); *A61B 5/14532* (2013.01); *A61B 5/332* (2021.01); *A61B 5/6893* (2013.01); *A61B 5/7475* (2013.01); *A61B 5/7495* (2013.01); *A61G 3/06* (2013.01); *A61G 3/061* (2013.01); *G06Q 10/1095* (2013.01); *G16H 10/20* (2018.01); *G16H 40/63* (2018.01); *A61B 5/021* (2013.01); *A61B 2503/08* (2013.01)

(58) Field of Classification Search
CPC ........ G16H 80/00; G16H 40/63; G16H 10/20; A61B 5/0006; A61B 5/0008; A61B 5/0013; A61B 5/0022
See application file for complete search history.

(56) References Cited

U.S. PATENT DOCUMENTS

| | | |
|---|---|---|
| 9,081,382 B2 | 7/2015 | Doyle |
| 10,043,396 B2 | 8/2018 | Salter |

(Continued)

OTHER PUBLICATIONS https://www.merriam-webster.com/dictionary/appointment.*
https://www.ahdictionary.com/word/search.html?q=appointment.*

*Primary Examiner* — Joseph M Dietrich
(74) *Attorney, Agent, or Firm* — SHEPPARD, MULLIN, RICHTER & HAMPTON LLP; Hector A. Agdeppa; Daniel N. Yannuzzi

(57) ABSTRACT

Exemplary implementations may: obtain passenger information related to a passenger that is relevant to an upcoming medical appointment; store such passenger information; and transmit such passenger information wirelessly to a caregiver with which the upcoming medical appointment is scheduled. Exemplary implementation also may: generate output signals conveying passenger information; provide one or more automated robotic assistants; determine the passenger information; determine necessity of deployment of the one or more automated robotic assistants; and deploy, based on the necessity of deployment, the one or more automated robotic assistants.

10 Claims, 4 Drawing Sheets

(51) Int. Cl.
    *A61B 5/145*     (2006.01)
    *A61B 5/01*     (2006.01)
    *G16H 10/20*     (2018.01)
    *A61B 5/332*     (2021.01)
    *A61B 5/021*     (2006.01)

(56) References Cited

U.S. PATENT DOCUMENTS

| | | | |
|---|---|---|---|
| 2014/0277894 A1* | 9/2014 | Doyle | B60W 10/26 |
| | | | 701/23 |
| 2018/0182055 A1 | 6/2018 | Jepson | |
| 2018/0196416 A1 | 7/2018 | Iagnemma | |
| 2018/0202822 A1 | 7/2018 | Delizio | |
| 2019/0052637 A1* | 2/2019 | Dean | H04W 12/04 |
| 2020/0128598 A1* | 4/2020 | Keller | H04W 84/005 |

* cited by examiner

SYSTEMS AND METHODS FOR ASSISTED TRANSPORTATION FOR MEDICAL CARE

TECHNICAL FIELD

The present disclosure relates to systems and methods for assisted transportation for medical care.

BACKGROUND

Frequent medical appointments may be necessary for some elderly and/or people with chronic medical conditions. However, due to the frequency of the medical appointments required, caretakers may not always have the time to transport such people to their appointments. Sending a transportation service to pick-up a person may cause caretakers to worry about the person's quality of care. Moreover, medical appointments may run long due to a series of preliminary tasks that must be completed for each patient.

BRIEF SUMMARY OF THE DISCLOSURE

The present invention discloses an autonomous vehicle configured to complete at least some preliminary tasks that must be necessary for medical appointments by obtaining passenger information while conveying the passenger to his/her upcoming medical appointment. Obtaining and transmitting the passenger information to the caretaker may lessen the time a passenger waits at a medical office. Additionally, the present invention discloses an autonomous vehicle that provides physical support, via automated robotic assistants, to passengers such that passengers do not have to struggle to and/or from a seat in the autonomous vehicle. The automated robotic assistants may be configured to deploy upon determination of deployment necessity such that caretakers may have peace of mind their loved ones are not struggling.

One aspect of the present disclosure relates to an autonomous vehicle configured to transport passengers to medical care and simultaneously eliminate the time spent at a medical location. The vehicle may include one or more passenger information units. The passenger information units may be configured to obtain passenger information related to a passenger that is relevant to an upcoming medical appointment. Obtaining such passenger information may be done while conveying the passenger to the upcoming medical appointment. The passenger information units may be configured to store such passenger information to electronic storage. Transmitters may be configured to transmit such passenger information wirelessly to a caregiver with which the upcoming medical appointment is scheduled. The vehicle may include one or more hardware processors configured by machine-readable instructions. The processor(s) may be configured to obtain request for passenger information of a passenger from a caregiver. The processor(s) may be configured to control such passenger information unit such that passenger information may be obtained. The processor(s) may be configured to assess the passenger information obtained for anomalies and handle accordingly.

Another aspect of the present disclosure relates to autonomous vehicle configured to provide physical support to passengers during transportation to and/or from the autonomous vehicle. Sensor(s) may be configured to generate output signals conveying passenger information. The system may include one or more hardware processors configured by machine-readable instructions. The processor(s) may be configured to determine, based on the output signals, the passenger information. The processor(s) may be configured to determine, based on the passenger information, necessity of deployment. The processor(s) may be configured to deploy, based on the necessity of deployment, one or more automated robotic assistants configured to provide support to a passenger during transportation to and/or from a seat in the vehicle. The one or more robotic assistants may be configured to provide a communication channel between the passenger and a caretaker of the passenger. The caretaker may include a family member, friend, spouse, and/or others. The communication channel may allow the passenger and the caretaker to converse during effectuation of the one or more automated robotic assistants. The communication channel may assist with providing comfort to the passenger.

Another aspect of the present disclosure relates to a method of transporting passengers to medical care and simultaneously eliminating the time spent at a medical office. The method may include obtaining passenger information related to a passenger that is relevant to an upcoming medical appointment. Obtaining such passenger information may be done while conveying the passenger to the upcoming medical appointment. The method may include storing such passenger information to electronic storage. The method may include transmitting such passenger information wirelessly to a caregiver with which the upcoming medical appointment is scheduled. The method may include obtaining a request for passenger information of a passenger from a caregiver. The method may include controlling a passenger information unit such that passenger information may be obtained. The method may include assessing the passenger information obtained for anomalies and handling accordingly.

Another aspect of the present disclosure relates to a method of providing physical support to passengers during transportation to and/or from the autonomous vehicle. The method may include generating output signals conveying passenger information. The method may include determining, based on the output signals, the passenger information. The method may include determining, based on the passenger information, necessity of deployment. The method may include deploying, based on the necessity of deployment, one or more automated robotic assistants configured to provide support to a passenger during transportation to and/or from a seat in the vehicle. The one or more robotic assistants may be configured to provide a communication channel between the passenger and a caretaker of the passenger. The caretaker may include a family member, friend, spouse, and/or others. The communication channel may allow the passenger and the caretaker to converse during effectuation of the one or more automated robotic assistants. The communication channel may assist with providing comfort to the passenger.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Figure 1:
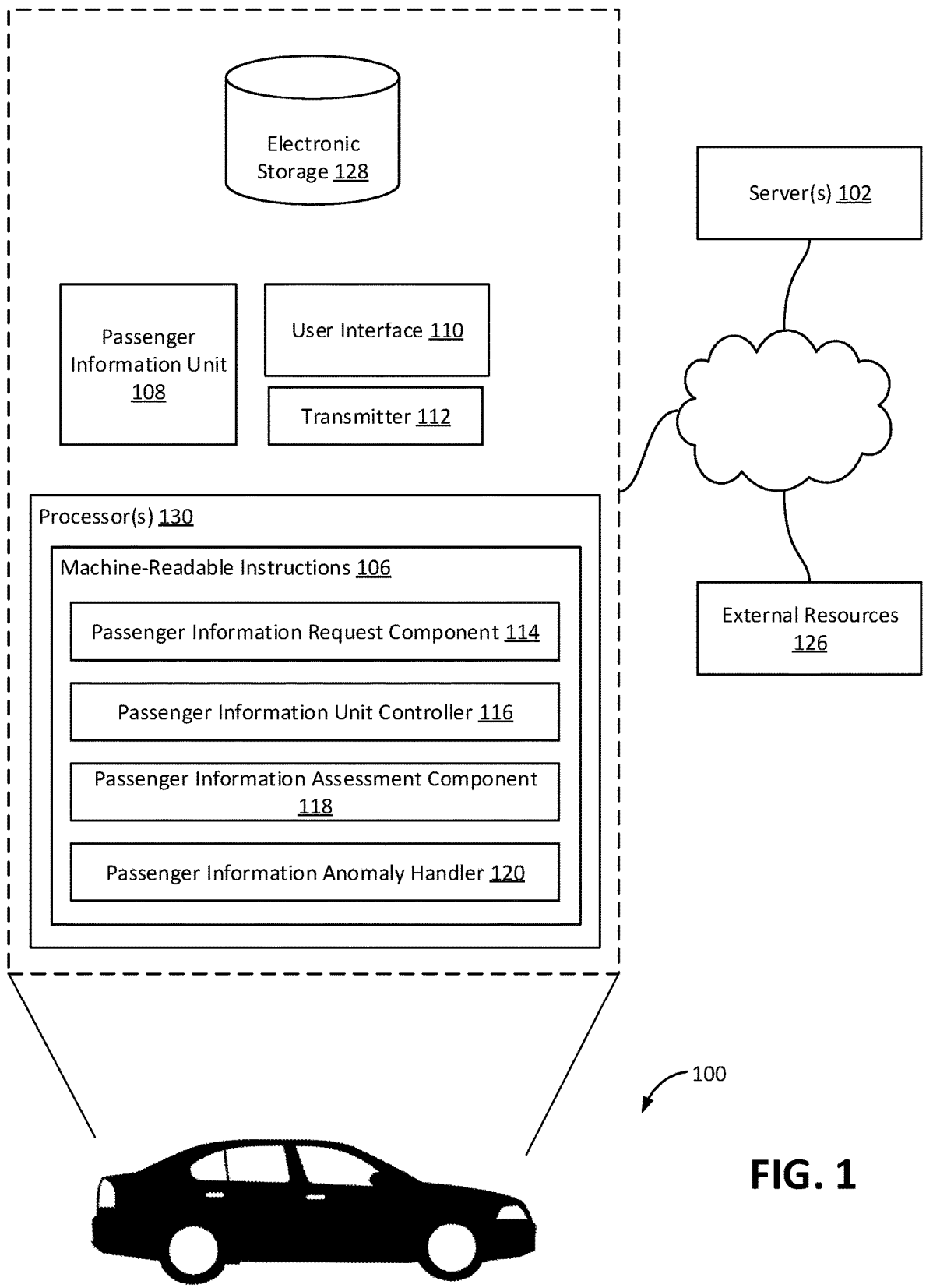
FIG. 1 illustrates an autonomous vehicle configured to obtain, store, and transmit passenger information while conveying a passenger to an upcoming medical appointment, in accordance with one or more implementations.

FIG. 1 illustrates vehicle(s) 100, in accordance with one or more implementations. In some implementations, vehicle(s) 100 may include one or more a passenger information unit 108, a user interface 110, and/or a transmitter 112.

Vehicle(s) 100 may be configured by machine-readable instructions 106. Machine-readable instructions 106 may include one or more instruction components. The instruction components may include computer program components. The instruction components may include one or more of passenger information request component 114, a passenger information unit controller 116, a passenger information assessment component 118, a passenger information anomaly handler 120, and/or other instruction components.

Passenger information unit 108 may be configured to obtain passenger information related to a passenger that is relevant to an upcoming medical appointment. Obtaining such passenger information may be done while conveying the passenger to the upcoming medical appointment. By way of non-limiting example, passenger information unit 108 may include a keyboard, a touchscreen, a microphone, an optical code reader, radio frequency identification reader (RFID), electronic ports, a fingerprint reader, one or more of a desktop computer, a laptop computer, a handheld computer, a tablet computing platform, a NetBook, a Smartphone, and/or other information reader devices. By way of non-limiting example passenger information unit 108 may include utilizing a blood pressure machine, a blood glucose meter, a thermometer, a portable electrocardiogram machine, scale, and/or other biometric apparatuses. Passenger information unit 108 may include a wireless communication and/or electronic ports receiver such that at least some of the upcoming appointment information may be received from an electronic mobile device of the passenger. A passenger may include an elderly person, person with disabilities, a person underaged, and/or other person who may require transportation to an upcoming medical appointment. An upcoming medical appointment may include reoccurring medical appointments, pre-operation check-ups, post-operation check-ups, a scheduled appointment, and/or other appointments.

Passenger information unit 108 may be configured to store such passenger information in electronic storage 128. Such passenger information may be stored temporarily until transmission to a caregiver is complete and/or in a long term manner.

Transmitter 112 may be configured to transmit such passenger information stored in electronic storage 128 wirelessly to a caregiver with which the upcoming medical appointment is scheduled. A caregiver may include a doctor's office, a medical office, a hospital, a clinic, and/or other caregiver. Transmitter 112 may also be configured to transmit a passenger information request such that passenger information request component 114 may generate and effectuate a request visible and/or audible by a passenger.

Passenger information request component 114 may be configured to obtain a passenger information request, via transmitter 112, for passenger information of a passenger that will be relevant to the upcoming medical appointment. The passenger information request may be from a caregiver related to the upcoming medical appointment. Passenger information request component 114 may generate and effectuate a request message and/or audio such that a passenger information request may be communicated to the passenger. The passenger information request may for identification information of the passenger to verify identity of the passenger, upcoming appointment information, biometric information and/or other passenger information. By way of non-limiting example, identification information may include the passenger's name, fingerprint, address, phone number, medical identification, social security number, and/or other identification information. The upcoming appointment information may include insurance information, health history information, and/or other information collected prior to medical appointments. By way of non-limiting example, insurance information may include what services are covered by insurance, what services are not covered by insurance, copay information, and/or other insurance information. By way of non-limiting example, the biometric information may include blood pressure, blood sugar, heart rhythm, body temperature, weight, and/or other biometric information.

User interface 110 may be configured to provide an interface between the passenger and the caregiver the request message and/or audio for the passenger generated by passenger information request component 114 is displayed and/or played. User interface 110 may include a screen, a touchscreen, audio speakers, and/or other devices to relay messages. User interface 110 may be visible and/or audible in vehicle 100 such that the passenger may receive messages and/or requests from caregivers for passenger information from passenger information unit 108. By way of non-limiting example, a caregiver at a medical office may send a request for a passenger to verify his/her identity. A message may appear on user interface 110 such that the passenger can hear and/or see his/her name being request for identity verification. The passenger may then make his/her way to passenger information unit 108.

Passenger information unit controller 116 may be configured to control the passenger information unit of the passenger in accordance with the passenger information request. Passenger information unit controller 116 may be configured to control passenger information unit such that passenger information unit 108 is prepared to obtain the passenger information that was requested. Preparation may include turning on relevant devices, checking if the relevant devices work, recalibrating the relevant devices, and/or other preparation. By way of non-limiting example, a passenger information request from a caregiver may be a request for biometric information. Passenger information unit controller 116 may prepare passenger information unit 108 to obtain biometric information and not, for example, verification information. Preparation may include turn on biometric reading devices, checking if the biometric reading devices work, recalibrating the biometric reading devices, and/or other preparation functions.

Passenger information assessment component 118 may be configured to assess such passenger information obtained by passenger information unit 108. Assessment may include comparing biometric information metrics to thresholds to check for passenger information anomalies. Passenger information anomalies may indicate medical emergencies such that conveyance to the caregiver and/or to a secondary caregiver should be expedited. The thresholds may include metrics relevant to individual patients, overall metrics indicative of medical emergencies, and/or other thresholds. By way of non-limiting example, an obtained blood glucose level of a passenger with diabetes may be considered a passenger information anomaly such that it reflects a dangerous level. By way of non-limiting example, an obtained blood glucose level of a passenger without diabetes may be not be considered a passenger information anomaly such that it reflects a previous sugary meal.

Passenger information anomaly handler 120 may be configured to, responsive to detecting a passenger information anomaly, effectuate one or more emergency responses. The passenger information anomaly may indicate a medical emergency. Emergency responses may include expedition of the conveyance to the upcoming medical appointment, effectuating notification of the passenger information anomaly to the caregiver, effectuating notification of the passenger information anomaly to a secondary caregiver, initiating an autonomous onboard response system, and/or other emergency responses. By way of non-limiting example, the expedition of the conveyance to the upcoming medical appointment may include rerouting to convey the passenger to the upcoming medical appointment before other passengers, activating lights, activating sirens, and/or other expedition actions. By way of non-limiting example, the secondary caregiver may include one or more of a paramedic, emergency medical technician (EMT), nearby hospital, police, loved one, and/or others.

Figure 2:
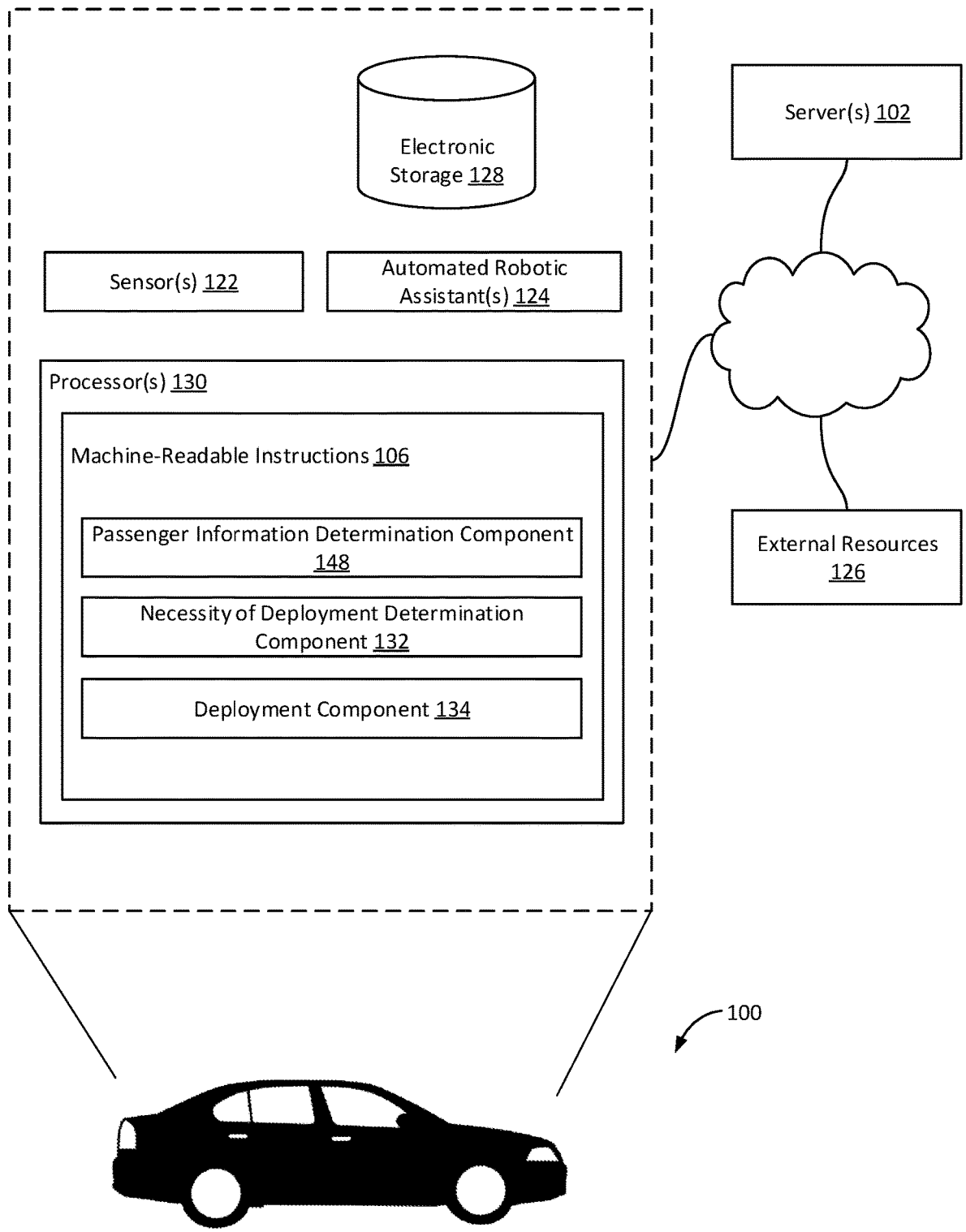
FIG. 2 illustrates an autonomous vehicle configured to provide physical support to a passenger during transportation to and/or from a seat in an autonomous vehicle, in accordance with one or more implementations.

FIG. 2 illustrates a vehicle 100, in accordance with one or more implementations. In some implementations, vehicle 100 may include one or more of sensor(s) 122 and/or automated robotic assistant(s) 124. In some implementations, vehicle 100 may include one or more of sensor(s) 122 and automated robotic assistant(s) 124 in addition to components of vehicle(s) 100 illustrated in FIG. 1.

Vehicle(s) 100 may be configured by machine-readable instructions 106. Machine-readable instructions 106 may include one or more instruction components. The instruction components may include computer program components. The instruction components may include one or more of passenger information determination component 148, a necessity of deployment determination component 132, a deployment component 134, and/or other instruction components.

Sensor(s) 122 may be configured to generate output signals conveying passenger information. The passenger information characterizes a passenger nearby the vehicle in which they will enter to convey him/her to an upcoming medical appointment. By way of non-limiting example, the passenger may be walking independently, in a manual wheel chair, in an electric wheel chair, wearing a cast and/or brace, transporting a long distance to and/or from the vehicle, traversing stairs to transport to and/from the vehicle, carrying one or more bags, linked with medical equipment, and/or others. By way of non-limiting medical equipment may include an oxygen tank, other respiratory equipment, an IV pole, and/or other medical equipment.

Sensor(s) 122 may include image sensors, cameras, and/or other sensors. As used herein, the terms "camera" and/or "image sensor" may include any device that captures images, including but not limited to a single lens-based camera, a camera array, a solid-state camera, a mechanical camera, a digital camera, an image sensor, a depth sensor, a remote sensor, a lidar, an infrared sensor, a (monochrome) complementary metal-oxide-semiconductor (CMOS) sensor, an active pixel sensor, and/or other sensors. Individual sensors may be configured to capture information, including but not limited to visual information, video information, audio information, geolocation information, orientation and/or motion information, depth information, and/or other information. Information captured by one or more sensors may be marked, timestamped, annotated, and/or otherwise processed such that information captured by other sensors can be synchronized, aligned, annotated, and/or otherwise associated therewith. For example, video information captured by an image sensor may be synchronized with information captured by an accelerometer or other sensor. Output signals generated by individual image sensors (and/or information based thereon) may be stored and/or transferred in electronic files.

Passenger information determination component 148 may be configured to determine passenger information. Passenger information may be based on generated the output signals. Passenger information may indicate a passenger's need for physical support during transportation to and/or from a seat in the vehicle. The passenger may be defined by parameter values for one or more passenger parameters. The passenger parameters may include one or more characteristics of a passenger (e.g., motion, age, relative position, distance from the vehicle, etc.), vocalization, present medical equipment, transportation means (e.g., manual wheel chair, electric wheel chair, walking cane, walker, etc.), preset deployment of the one or more automated robotic assistants by a caretaker of the passenger, and/or others. By way of non-limiting example, the passenger is defined by passenger parameters, wherein the passenger parameters may include the passenger's age, distance from the vehicle, transportation means, motion, and preset deployment of automated robotic assistants. The parameter values for the passenger parameters may include 78 years old, 20 feet away from the vehicle, walking, has no transportation means, motion is slow, and no preset deployment of automated robotic assistants, respectively.

Necessity of deployment determination component 132 may be configured to determine whether or not to deploy one or more automated robotic assistants to provide physical support to the passenger when transporting to and/or from a seat in the vehicle. Determination may be based on the values for the passenger parameters. Determination may be that one or more of the values of the passenger parameters have, for example, met thresholds requirements for deployment. Determination, by way of non-limiting example, may be based on a passenger vocalizing "I need help" such that it is determined that one or more automated robotic assistants should be deployed, regardless of other values for the passenger parameters.

Deployment component 134 may configured to deploy the one or more automated robotic assistants. Deployment may be based on the necessity of deployment determination such that it is determined that a passenger needs physical support with transportation, e.g., walking, stepping into the vehicle, finding an open seat in the vehicle, etc.

Automated robotic assistant(s) 124 may be configured to provide physical support to a passenger during transportation to and/or from a seat in the vehicle. Automated robotic assistant(s) 124 may include a deployable ramp, hand rail, autonomous cane, autonomous walker, and/or others. Automated robotic assistant(s) 124 may also be configured to provide a communication channel between the passenger and a caretaker of the passenger such that the passenger and the caretaker can converse during effectuation of the one or more automated robotic assistants. The communication channel may include audio and/or video communication (i.e., a phone call and/or video call). The caretaker of the passenger may include the medical office in which the upcoming medical appointment is, a family member, a friend, and/or others. Conversation between the passenger and the caretaker may provide more comfort to the passenger as the enter and/or exit the vehicle to and/or from the upcoming medical appointment. Automated robotic assistant(s) 124 may also be configured to capture and send imaging information of the passenger to the caretaker such that the caretaker has confirmation the passenger is conveying to and/or from the medical appointment. Imaging information may be based on one or more sensors present on the automated robotic assistant. Imaging information may include a picture, a series of pictures, a video clip, and/or other imaging information.

In some implementations, vehicle(s) 100, and/or external resources 126 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which vehicle(s) 100, and/or external resources 126 may be operatively linked via some other communication media.

External resources 126 may include sources of information outside of vehicle 100, external entities participating with vehicle 100, and/or other resources. In some implementations, some or all of the functionality attributed herein to external resources 126 may be provided by resources included in vehicle 100.

Vehicle(s) 100 may include electronic storage 128, one or more processors 130, and/or other components. Vehicle(s) 100 may include communication lines, or ports to enable the exchange of information with a network and/or other computing platforms. Illustration of vehicle(s) 100 in FIG. 1 and FIG. 2 are not intended to be limiting. Vehicle(s) 100 may include a plurality of hardware, software, and/or firmware components operating together to provide the functionality attributed herein to vehicle(s) 100. For example, vehicle(s) 100 may be implemented by a cloud of computing platforms operating together as vehicle(s) 100.

Electronic storage 128 may comprise non-transitory storage media that electronically stores information. The electronic storage media of electronic storage 128 may include one or both of system storage that is provided integrally (i.e., substantially non-removable) with vehicle(s) 100 and/or removable storage that is removably connectable to vehicle(s) 100 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from vehicle(s) 100, information received from vehicle(s) 100, and/or other information that enables vehicle(s) 100 to function as described herein.

Processor(s) 130 may be configured to provide information processing capabilities in vehicle(s) 100. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 and FIG. 2 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 114, 116, 118, 120, 132, 134, and/or 148, and/or other components. Processor(s) 130 may be configured to execute components 114, 116, 118, 120, 132, 134, and/or 148, and/or other components by software; hardware; firmware; some combination of software, hardware, and/or firmware; and/or other mechanisms for configuring processing capabilities on processor(s) 130. Some or all components 114, 116, 118, 120, 132, 134, and/or 148, and/or other components may be executed by server(s) 102. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 114, 116, 118, 120, 132, 134, and/or 148 are illustrated in FIG. 1 and FIG. 2 as being implemented within a single processing unit, in implementations in which processor(s) 130 includes multiple processing units, one or more of components 114, 116, 118, 120, 132, 134, and/or 148 may be implemented remotely from the other components. The description of the functionality provided by the different components 114, 116, 118, 120, 132, 134, and/or 148 described below is for illustrative purposes, and is not intended to be limiting, as any of components 114, 116, 118, 120, 132, 134, and/or 148 may provide more or less functionality than is described. For example, one or more of components 114, 116, 118, 120, 132, 134, and/or 148 may be eliminated, and some or all of its functionality may be provided by other ones of components 114, 116, 118, 120, 132, 134, and/or 148. As another example, processor(s) 130 may be configured to execute one or more additional components that may perform some or all of the functionality attributed below to one of components 114, 116, 118, 120, 132, 134, and/or 148.

Figure 3:
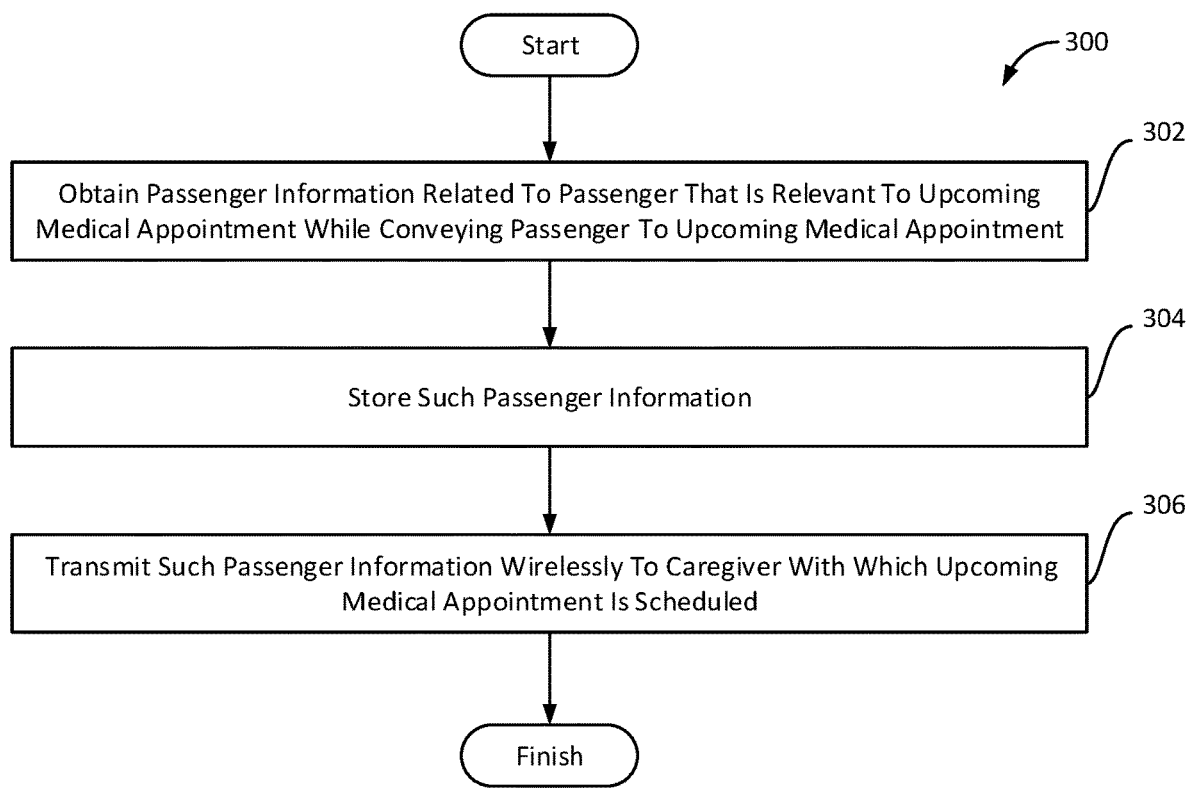
FIG. 3 illustrates a method of obtaining, storing, and transmitting passenger information while conveying a passenger to an upcoming medical appointment, in accordance with one or more implementations.

FIG. 3 illustrates a method 300 for obtaining, storing, and transmitting passenger information while conveying a passenger to an upcoming medical appointment, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

An operation 302 may include obtaining passenger information related to a passenger that is relevant to an upcoming medical appointment. Obtaining such passenger information may be done while conveying the passenger to the upcoming medical appointment. Such passenger information may include verification information, upcoming medical appointment information, biometric information, and/or other passenger information. Operation 302 may be performed by one or more hardware processors configured by machine-readable instructions including a component that is the same as or similar to passenger information unit 108, in accordance with one or more implementations.

An operation 304 may include storing such passenger information. Storing such passenger information may be temporary such that transmission of such passenger information to a caregiver has not completed yet. Operation 304 may be performed by one or more hardware processors configured by machine-readable instructions including a component that is the same as or similar to passenger information unit 108 and storing to electronic storage 128, in accordance with one or more implementations.

An operation 306 may include transmitting such passenger information wirelessly to a caregiver with which the upcoming medical appointment is scheduled. Operation 306 may be performed by one or more hardware processors configured by machine-readable instructions including a component that is the same as or similar to transmitter 112, in accordance with one or more implementations.

Figure 4:
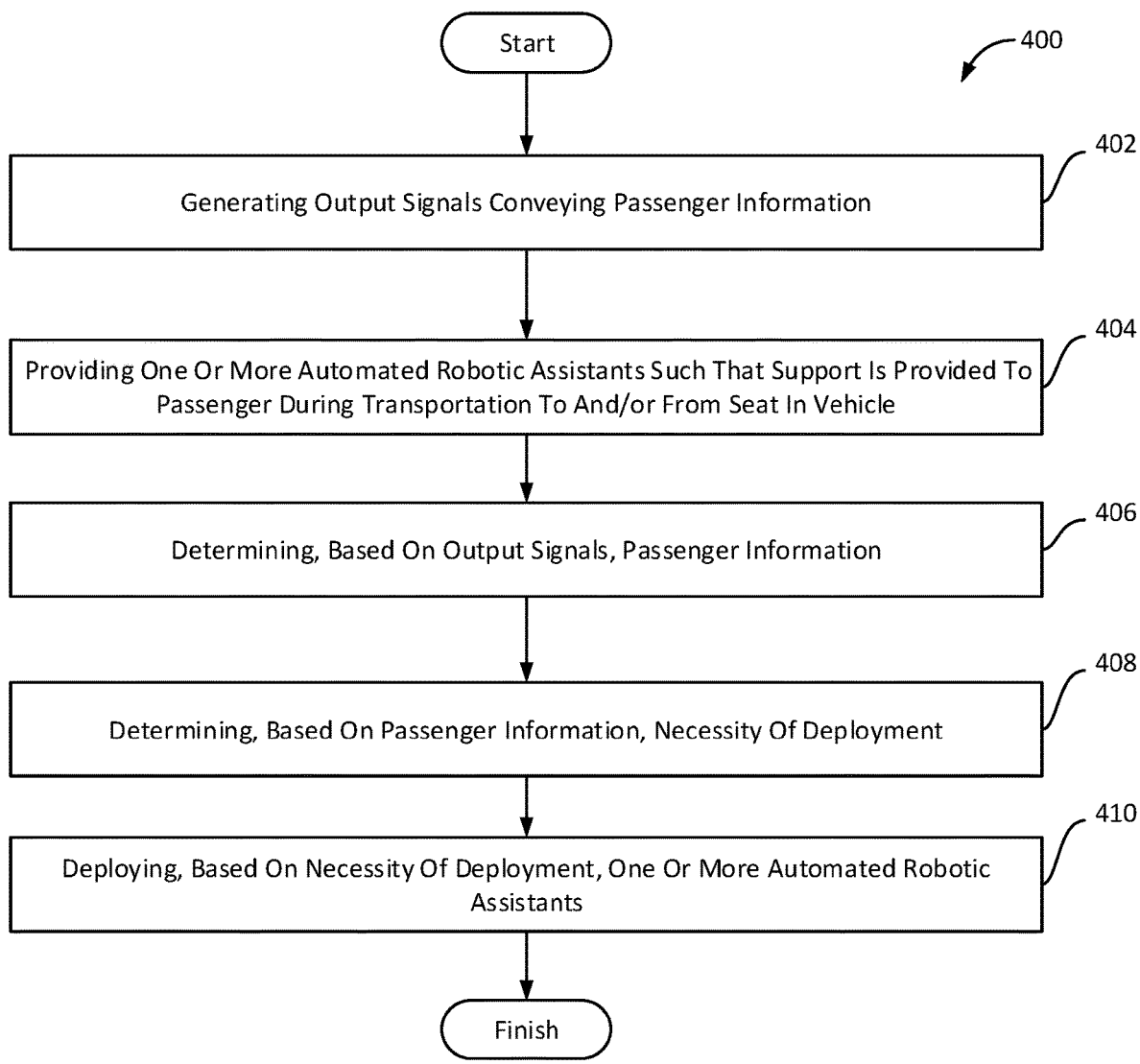
FIG. 4 illustrates a method of providing physical support to a passenger during transportation to and/or from a seat in an autonomous vehicle, in accordance with one or more implementations.

FIG. 4 illustrates a method 400 for providing physical support to passengers during transportation to and/or from an autonomous vehicle, in accordance with one or more implementations. The operations of method 400 presented below are intended to be illustrative. In some implementations, method 400 may be accomplished with one or more additional operations not described, and/or without one or more of the operations discussed. Additionally, the order in which the operations of method 400 are illustrated in FIG. 4 and described below is not intended to be limiting.

In some implementations, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

An operation 402 may include generating output signals conveying passenger information. Operation 402 may be performed by one or more components that is the same as or similar to sensor(s) 122, in accordance with one or more implementations.

An operation 404 may include providing one or more automated robotic assistants such that support is provided to a passenger during transportation to and/or from a seat in the vehicle. Operation 404 may be performed by one or more components that is the same as or similar to automated robotic assistant(s) 124, in accordance with one or more implementations.

An operation 406 may include determining, based on the output signals, the passenger information. The passenger information may characterize a passenger nearby the vehicle in which they will enter to convey him/her to an upcoming medical appointment. The passenger information may be indicative of whether or not the passenger needs physical support when transporting to/from a seat in the vehicle. Operation 406 may be performed by one or more hardware processors configured by machine-readable instructions including a component that is the same as or similar to passenger information determination component 148, in accordance with one or more implementations.

An operation 408 may include determining, based on the passenger information, necessity of deployment. Determination is whether or not to deploy one or more automated robotic assistants. Determination may be based on parameter values of passenger parameters that define a passenger. Operation 408 may be performed by one or more hardware processors configured by machine-readable instructions including a component that is the same as or similar to necessity of deployment determination component 132, in accordance with one or more implementations.

An operation 410 may include deploying, based on the necessity of deployment, one or more automated robotic assistants. Operation 410 may be performed by one or more hardware processors configured by machine-readable instructions including a component that is the same as or similar to deployment component 134, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. An autonomous automotive vehicle, comprising:
   a passenger information unit configured to obtain passenger information related to a passenger that is relevant to an upcoming medical appointment, wherein the passenger information unit is further configured to obtain such passenger information while conveying the passenger to the upcoming medical appointment;

electronic storage configured to store such passenger information; and a transmitter configured to transmit such passenger information wirelessly to a caregiver with which the upcoming medical appointment is scheduled.

2. The autonomous automotive vehicle of claim 1, wherein the vehicle further comprises:

a user interface configured to provide an interface between the passenger and the caregiver;

one or more processors configured by machine-readable instructions to:

obtain a passenger information request, via the transmitter, for the passenger information of the passenger that will be relevant to the upcoming medical appointment;

control the user interface to communicate the passenger information request to the passenger; and control the passenger information unit to obtain the passenger information of the passenger in accordance with the passenger information request.

3. The autonomous automotive vehicle of claim 2, wherein the one or more processors are further configured by machine readable instructions to:

assess such passenger information; and responsive to detecting a passenger information anomaly, effectuate one or more of (i) expedition of the conveyance to the upcoming medical appointment; (ii) effectuate notification of the passenger information anomaly to the caregiver; (iii) effectuate notification of the passenger information anomaly to a secondary caregiver; and/or (iv) initiate an autonomous onboard response system.

4. The autonomous automotive vehicle of claim 1, wherein the passenger information unit includes a keyboard, a touchscreen, a microphone, an optical code reader, a radio frequency identification reader (RFID), an electronic port, a fingerprint reader, a wireless receiver, a blood pressure machine, a blood glucose meter, a thermometer, a portable electrocardiogram (ECG) machine, and/or a scale.

5. The autonomous automotive vehicle of claim 4, wherein the passenger information unit is further configured to obtain identification information of the passenger to verify identity of the passenger, upcoming appointment information, and/or biometric information, wherein the identification information includes the passenger's name, fingerprint, address, phone number, medical identification, and/or social security number, wherein the upcoming appointment information includes insurance information and/or health history information, wherein the biometric information includes blood pressure, blood sugar, heart rhythm, body temperature, and/or weight.

6. A method, comprising:

obtaining passenger information related to a passenger that is relevant to an upcoming medical appointment, wherein obtaining such passenger information is done while conveying the passenger to the upcoming medical appointment in an autonomous automotive vehicle;

storing such passenger information; and transmitting such passenger information wirelessly to a caregiver with which the upcoming medical appointment is scheduled.

7. The method of claim 6, further comprising:

providing, by a user interface, an interface between the passenger and the caregiver;

obtaining a passenger information request for the passenger information of the passenger that will be relevant to the upcoming medical appointment;

controlling the user interface to communicate the passenger information request to the passenger; and controlling obtainment of the passenger information of the passenger in accordance with the passenger information request.

8. The method of claim 7, further comprising:

assessing such passenger information; and responsive to detecting a passenger information anomaly, effectuating one or more of (i) expedition of the conveyance to the upcoming medical appointment; (ii) effectuating notification of the passenger information anomaly to the caregiver; (iii) effectuating notification of the passenger information anomaly to a secondary caregiver; and/or (iv) initiating an autonomous onboard response system.

9. The method of claim 6, wherein the obtaining the passenger information includes utilizing a keyboard, a touchscreen, a microphone, an optical code reader, radio frequency identification reader (RFID), electronic port, a fingerprint reader, a wireless receiver, a blood pressure machine, a blood glucose meter, a thermometer, a portable electrocardiogram (ECG) machine, and/or scale.

10. The method of claim 9, wherein the obtaining the passenger information includes obtaining identification information of the passenger to verify identity of the passenger, upcoming appointment information, and/or biometric information, wherein identification information includes the passenger's name, fingerprint, address, phone number, medical identification, and/or social security number, wherein the upcoming appointment information includes insurance information and/or health history information, wherein the biometric information includes blood pressure, blood sugar, heart rhythm, body temperature, and/or weight.

* * * * *